United States Patent
Beaudry et al.

(10) Patent No.: US 12,128,073 B2
(45) Date of Patent: *Oct. 29, 2024

(54) CANINE-SPECIFIC THERAPEUTIC COMPOSITIONS AND METHODS OF USE

(71) Applicant: AlphaLogix, LLC, Phoenix, AZ (US)

(72) Inventors: Christian Beaudry, Phoenix, AZ (US); Jaehyun Kim, Phoenix, AZ (US)

(73) Assignee: ALPHALOGIX, LLC, Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/056,145

(22) Filed: Nov. 16, 2022

(65) Prior Publication Data
US 2023/0149472 A1 May 18, 2023

Related U.S. Application Data

(60) Provisional application No. 63/280,024, filed on Nov. 16, 2021.

(51) Int. Cl.
*A61K 35/50* (2015.01)
(52) U.S. Cl.
CPC .................... *A61K 35/50* (2013.01)
(58) Field of Classification Search
None
See application file for complete search history.

(56) References Cited

U.S. PATENT DOCUMENTS

| | | | | |
|---|---|---|---|---|
| 9,132,156 B1 * | 9/2015 | Werber | ............... | A61K 8/982 |
| 10,363,278 B2 * | 7/2019 | Beaudry | ............. | C12N 5/0605 |
| 11,207,355 B2 * | 12/2021 | Beaudry | ................ | A61K 35/35 |
| 11,707,492 B2 * | 7/2023 | Tseng | .................... | A61L 27/367 |
| | | | | 424/93.7 |
| 2008/0069895 A1 | 3/2008 | Liu et al. | | |
| 2013/0078221 A1 | 3/2013 | Kang et al. | | |
| 2018/0126036 A1 | 5/2018 | Early | | |

(Continued)

FOREIGN PATENT DOCUMENTS

| | | | | |
|---|---|---|---|---|
| CN | 105521523 A | * | 4/2016 | |
| LV | 12919 B | * | 3/2003 | |

OTHER PUBLICATIONS

Geisert, T. E. Spencer (eds.), Placentation in Mammals, Advances in Anatomy, Embryology and Cell Biology 234 (Year: 2021).*

(Continued)

*Primary Examiner* — Arthur S Leonard
*Assistant Examiner* — Briana N Ebbinghaus
(74) *Attorney, Agent, or Firm* — NGUYEN TARBET IP LAW

(57) ABSTRACT

The present invention has developed methods of producing a canine-specific therapeutic composition that is clear, safe, and physiologically and biologically active liquid injectable. The tissue processing protocols described herein include methods for processing and cleaning the incoming dark green placentas to produce a clear amnion injectable product while maintaining its physiological and biological properties. Thus, the present invention features canine-specific therapeutic compositions comprising placental-derived materials and methods of use.

17 Claims, 11 Drawing Sheets
(8 of 11 Drawing Sheet(s) Filed in Color)

(56) References Cited

U.S. PATENT DOCUMENTS

2021/0269775 A1  9/2021  Zhang et al.

OTHER PUBLICATIONS

Park et al. Isolation and Characterization of Canine Amniotic Membrane-Derived Multipotent Stem Cells. PLoS One. 2012; 7(9): e44693 (Year: 2012).*
Mirabel et al. Stability enhancement of clinical grade multipotent mesenchymal stromal cell-based products. J Transl Med. Oct. 24, 2018;16(1):291 (Year: 2018).*
Fleck et al. Modern Collagen Wound Dressings: Function and Purpose. J Am Col Certif Wound Spec. Sep. 2010; 2(3): 50-54. (Year: 2010).*

* cited by examiner

Canine term fetus

FIG. 3

| Layer | Extracellular-Matrix Composition |
|---|---|
| Amnion | |
| Epithelium | Single layer, cuboidal with microvilli |
| Basement membrane | Collagen types III, IV, V; laminin, fibronectin, nidogen |
| Compact layer | Collagen types I, III, V, VI; fibronectin |
| Fibroblast layer | Collagen types I, III, VI; nidogen, laminin, fibronectin |
| Intermediate (spongy) layer | Collagen types I, III, IV; proteoglycans |
| Chorion | |
| Reticular layer | Collagen types I, III, IV, V, VI; proteoglycans |
| Basement membrane | Collagen type IV; fibronectin, laminin |
| Trophoblasts | |

//

CANINE-SPECIFIC THERAPEUTIC COMPOSITIONS AND METHODS OF USE

CROSS-REFERENCES TO RELATED APPLICATIONS

This application is a non-provisional and claims benefit of U.S. Provisional Application No. 63/280,024 filed Nov. 16, 2021, the specification(s) of which is/are incorporated herein in their entirety by reference.

FIELD OF THE INVENTION

The present invention features canine-specific therapeutic compositions comprising placental-derived materials and methods of use.

BACKGROUND OF THE INVENTION

Dogs are members of the group of species that have zonary placentas meaning that multiple placentas are contained within the uterus. Each placenta is comprised of two distinct sacs, the chorioallantoic sac which is the outer sac containing allantoic fluid and the amnion sac which is the inner sac containing the amniotic fluid and fetus. The placentas are attached to the uterus wall at the hematophagus zones (marginal hematomas). These are bands of maternal hemorrhage at the margins of the zonary placenta. The products of hemoglobin breakdown give a distinct green tissue coloration. Upon detachment of the placentas from the uterine wall, a dark green discharge (sometimes called uteroverdin) is produced which stains the placentas dark green which makes the tissue very problematic for processing.

This dark green color partially represents the presence of contaminants, particularly blood-related contaminants. The presence of blood-related contaminants, indicated by dark green coloration, may trigger alloimmunization responses in canine allograft recipients, thus harming the recipient and/or causing graft failure, decreasing or negating the therapeutic effects of the allograft materials. Removal of contaminants, especially blood-related contaminants, evidenced in part by removal of dark green coloration, is a desirable outcome that has not yet been achieved in the prior art but is achieved by the present invention. Removal of contaminants allows genetically non-identical canine patient-recipients to receive allografts more safely and effectively, as the risk of alloimmunization reaction and graft rejection are reduced or eliminated.

The present invention has developed tissue recovery and tissue processing protocols where placentas are recovered during live births or scheduled c-sections, shipped under controlled temperature, and processed into a clear liquid biological product substantially free of contaminants, especially blood-related contaminants, that can be safely administered in dogs, including dogs that are not genetically identical to the donor (i.e., allograft recipients). The tissue processing protocol include methods for processing and cleaning the incoming dark green placentas to produce a clear amnion injectable product while maintaining its physiological and biological properties.

BRIEF SUMMARY OF THE INVENTION

It is an objective of the present invention to provide compositions and methods that allow for the production of a clear, safe, and physiologically and biologically active liquid injectable product (i.e., a canine-specific therapeutic composition) for use as a regenerative product in dogs with joint diseases, soft tissue lesions, inflammatory diseases, immunological diseases, cancer, neurological diseases, scarring, burns, wounds, eye ulcers, nerve injuries, muscle tears, organ diseases, among others, as specified in the independent claims. The present invention may also be administered via other routes of administration in other embodiments, for example, topically. Embodiments of the invention are given in the dependent claims. Embodiments of the present invention can be freely combined with each other if they are not mutually exclusive.

In some embodiments, the present invention features a canine-specific therapeutic composition. In some embodiments, the composition comprises placental tissue in a working solution. In other embodiments, the placental tissue is canine-specific placental tissue. In some embodiments, the placental tissue comprises an allantoamnion, an chorioallantois, or a combination thereof.

In other embodiments, the present invention may further feature a method of producing a canine-specific therapeutic composition. In some embodiments, the method comprises obtaining a whole canine placenta. In some embodiments, the method comprises dissecting the whole canine placenta and retaining an allantoamnion membrane. In some embodiments, the method comprises rinsing the allantoamnion membrane and drying the allantoamnion membrane. In some embodiments, the method comprises micronizing the aforementioned allantoamnion membrane and resuspending the micronized allantoamnion membrane into a working solution to create a canine-specific therapeutic composition. In other embodiments, the method further comprises freezing the canine-specific therapeutic composition to preserve proteins.

In further embodiments, the present invention may further feature a method of treating or preventing cancer in a canine. In some embodiments, the method comprises administering a therapeutic amount of canine-specific therapeutic composition comprising placental tissue and a working solution.

One of the unique and inventive technical features of the present invention is the retention and use of all layers in the allantoamnion membrane. Without wishing to limit the invention to any theory or mechanism, it is believed that the technical feature of the present invention advantageously provides for a canine-specific therapeutic composition comprising a high concentration of proteins. Human fetal membrane is derived from the inner and outer layers of a single amniotic sac and is comprised of two conjoined membranes- amnion and chorion. The amnion faces the fetus and the chorion faces the uterus. In dogs, the amnion membrane is part of the allantoamnion sac which contains the fetus and amniotic fluid and the chorion membrane is part of the chorionallantois sac which contains the allantoic fluid. The histological representation of the canine allantoamnion membrane is distinct from the human amnion membrane. The allantoamnion membrane comprises an epithelium layer and a basement membrane layer on both sides of a stromal layer. The allantoamnion membrane composition comprises cells, cellular excretions, cellular derivatives, and extracellular matrix components. The allantoamnion membrane is not attached to the chorionallantois unlike the human amnion and chorion membranes. Therefore, canine-specific therapeutic compositions described herein are distinct and unique. None of the presently known prior references or work has the unique inventive technical feature of the present invention. For example, there are no other therapeutic compositions that utilize the allantoamnion membrane specifically from a canine.

Another of the unique and inventive technical features of the present invention is the ability to not only retain and use all layers in the allantoamnion membrane, but to do so while also substantially removing immunogenic contaminants. Removal of immunogenic contaminants, particularly blood-related contaminants, is accompanied by creation of a substantially clear and colorless product, including upon suspension in a working solution. Without wishing to limit the present invention to any particular theory or mechanism, it is believed that the technical feature of the present invention advantageously provides for a high concentration of proteins while removing components that may elicit an alloimmunization response when introduced into a canine patient. Blood group antigens are one of the major classes of alloantigens. Multiple potentially immunogenic contaminants, including blood-derived contaminants are advantageously removed with the present invention. A byproduct of this process is that the final allograft product of this invention is a colorless, clear or cloudy suspension, as compared to prior art approaches which have been unable to produce a product substantially free of the characteristic dark green color of the canine placenta. As this dark green color is the result of the breakdown of bilirubin, a product of heme catabolism, production of a colorless product is a byproduct of the present invention's inventive feature that allows removal of immunogenic contaminants, especially blood-related contaminants. Without wishing to limit the present invention to any particular theory or mechanism, it is believed that the technical feature of the present invention therefore provides for increased safety and efficacy by reducing the chance that a recipient of the canine allograft develops an alloimmune response. Safety is increased as alloimmune responses can result in transfusion reactions, graft rejection, and other harmful adverse effects that may harm the canine patient directly. Furthermore, efficacy is also increased, as the likelihood of graft rejection is greatly reduced, therefore increasing the chance that the allograft is able to exert a therapeutic effect on the canine patient-recipient.

Furthermore, the inventive technical features of the present invention contributed to a surprising result. For example, the present invention does not utilize a transport solution (i.e., a saline solution) to transport the whole canine placenta obtained. Surprisingly, it was discovered that approximately 40% more proteins are retained in the membrane of the placenta when transported without a transport solution (i.e., a saline solution). Without wishing to limit the present invention to any particular theory or mechanism, it is believed that the technical feature of the present invention therefore provides for greater efficacy by maintaining a greater amount of usable protein in the allograft product than previous approaches. Additionally, prior references teach away from the present invention as others utilize a saline solution to transport placentas and/or amniotic membrane pieces.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which:

FIG. 3 shows the different layers of the human amniotic membrane.

DETAILED DESCRIPTION OF THE INVENTION

Figure 1:
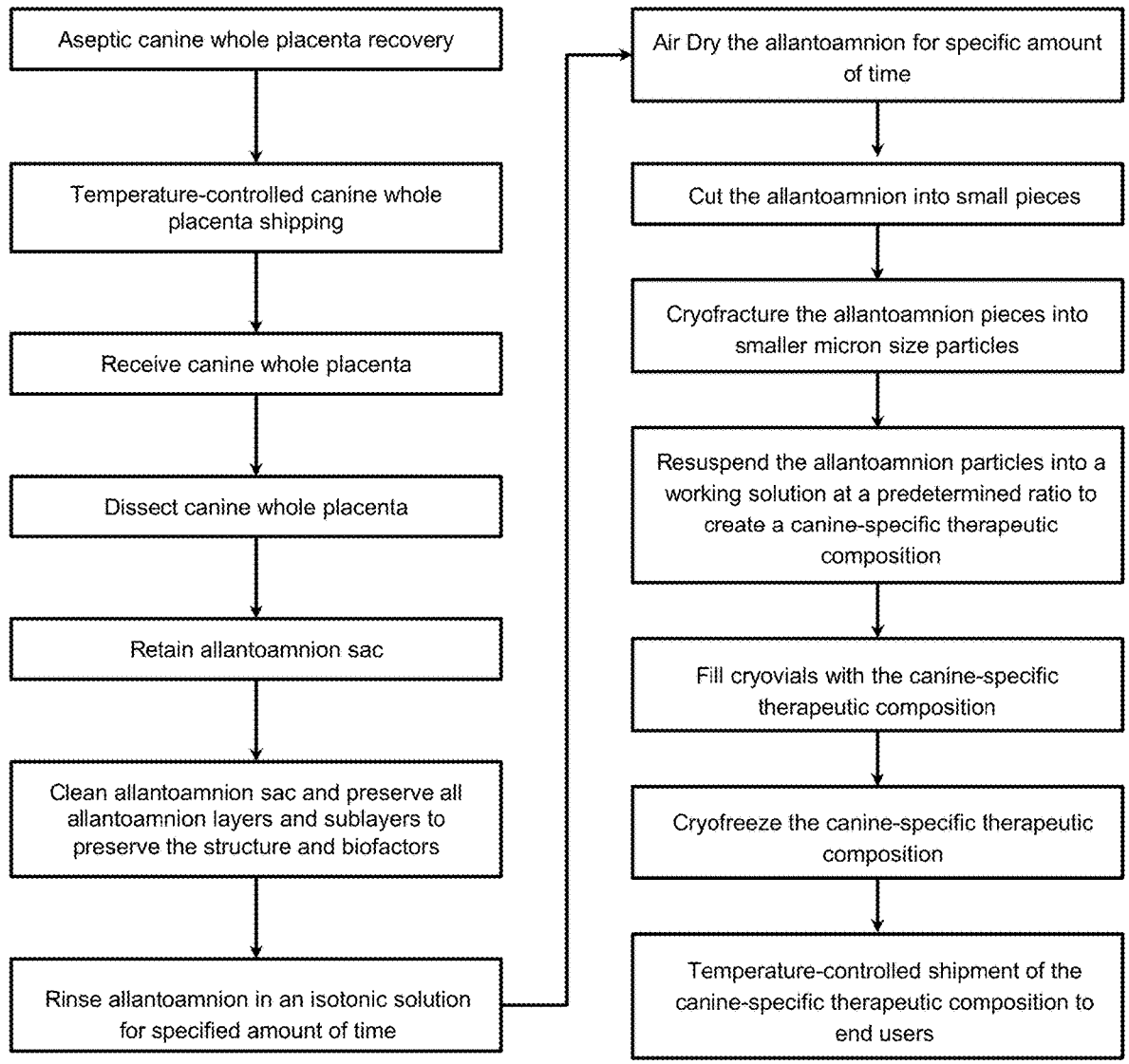
FIG. 1 shows a methodology of creating a canine-specific therapeutic composition described herein.

For purposes of summarizing the disclosure, certain aspects, advantages, and novel features of the disclosure are described herein. It is to be understood that not necessarily all such advantages may be achieved in accordance with any particular embodiments of the disclosure. Thus, the disclosure may be embodied or carried out in a manner that achieves or optimizes one advantage or group of advantages as taught herein without necessarily achieving other advantages as may be taught or suggested herein.

Additionally, although embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. Moreover, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described herein.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Placental tissue, as used herein, refers to tissues derived from a placenta including amnion membrane (i.e., allantoamnion), chorion membrane (i.e., chorioallantois), Wharton's Jelly, umbilical cord, and the like.

As used herein, "allantoamnion," "amnion membrane," "allantoamnion membrane," and "amnion" can be used interchangeably and refer to the inner sac comprising the amniotic fluid and fetus.

As used herein, "chorioallantois," "chorion membrane," "chorioallantois membrane," and "chorion" can be used interchangeably and refer to the outer sac comprising the allantoic fluid.

Micronized placental tissue particles, as used herein, are defined as particles derived from placenta including the allantoamnion, the chorioallantois or the umbilical cord. Allantoamnion particles may be preferred for therapeutics effectiveness. Placental tissue may be micronized to have an average particle size of about 100 μm in length, width, or thickness, and is preferably micronized to have an average particle size of about 10 μm in length, width, or thickness. In some embodiments, the placental tissue may be micronized to have an average particle size of about 2000 μm, or about 1800 μm, or about 1500 μm, or about 1250 μm, or about 1000 μm, or about 900 μm, or about 800 μm, or about 700 μm, or about 600 μm, or about 500 μm, or about 450 μm, or about 400 μm, or about 350 μm, or about 300 μm, or about 250 μm, or about 200 μm, or about 150 μm, or about 100 μm, or about 75 μm, or about 50 μm, or about 25, or about 10 μm, or about 5 μm, or about 1 μm, or about 0.5 μm, or about 0.1 μm and any range between and including the average particle sizes provided. Particle size, average particle size, or particle size distribution may be determined by analysis of scanning electron micrographs, or other suitable methods. Micronized placental tissue particles may be formed through any suitable method including, but not limited to, tissue grinding, cryogenic fracturing, application of heat and pressure, sonication and/or enzyme digestion. The resulting particles may be either used wet, partially dehydrated or essentially dehydrated by any means known to one of skill in the art such as, for example, lyophilization.

The terms "treating" or "treatment" refer to any indicia of success or amelioration of the progression, severity, and/or duration of a disease, pathology, or condition, including any objective or subjective parameter such as abatement; remission; diminishing of symptoms or making the injury, pathology or condition more tolerable to the patient; slowing in the rate of degeneration or decline; making the final point of degeneration less debilitating; disease modification; or improving a patient's physical or mental well-being.

The terms "manage," "managing," and "management" refer to preventing or slowing the progression, spread, or worsening of a disease or disorder, or of one or more symptoms thereof. In certain cases, the beneficial effects that a subject derives from a prophylactic or therapeutic agent do not result in a cure of the disease or disorder.

The term "effective amount" as used herein refers to the amount of a pharmaceutical, therapy, or medication which is sufficient to reduce and/or ameliorate the severity and/or duration of a given disease, disorder, or condition and/or a symptom related thereto. This term also encompasses an amount necessary for the reduction or amelioration of the advancement or progression of a given disease (e.g., cancer), disorder or condition, reduction or amelioration of the recurrence, development or onset of a given disease, disorder or condition, and/or to improve or enhance the prophylactic or therapeutic effect(s) of another therapy. In some embodiments, "effective amount" as used herein also refers to the amount of therapy provided herein to achieve a specified result.

As used herein, and unless otherwise specified, the term "therapeutically effective amount" is an amount sufficient enough to provide a therapeutic benefit in the treatment or management of a disease, or to delay or minimize one or more symptoms associated with the presence of a given disease. A therapeutically effective amount of an agent means an amount of therapeutic agent, alone or in combination with other therapies, which provides a therapeutic benefit in the treatment or management of the disease. The term "therapeutically effective amount" can encompass an amount that improves overall therapy, reduces or avoids symptoms or causes of a given disease, or enhances the therapeutic efficacy of another therapeutic agent.

The terms "administering", and "administration" refer to methods of providing a pharmaceutical, therapy, or medication preparation to a subject. Such methods are well known to those skilled in the art and include, but are not limited to, administering the compositions orally, intranasally, parenterally (e.g., intravenously and subcutaneously), by intramuscular injection, intra articular injection, intraligamentary injection, intratendon injection, by intraperitoneal injection, intrathecally, transdermally, extracorporeally, topically or the like.

The term "protein" as used herein can be the full length polypeptide, or a fragment or segment of a polypeptide, and can encompass a stretch of amino acids residues of at least about 8 amino acids, generally at least 10 amino acids, more generally at least 20 amino acids, often at least 30 amino acids, more often at least 50 amino acids or more of the full length polypeptide.

Figure 2A:
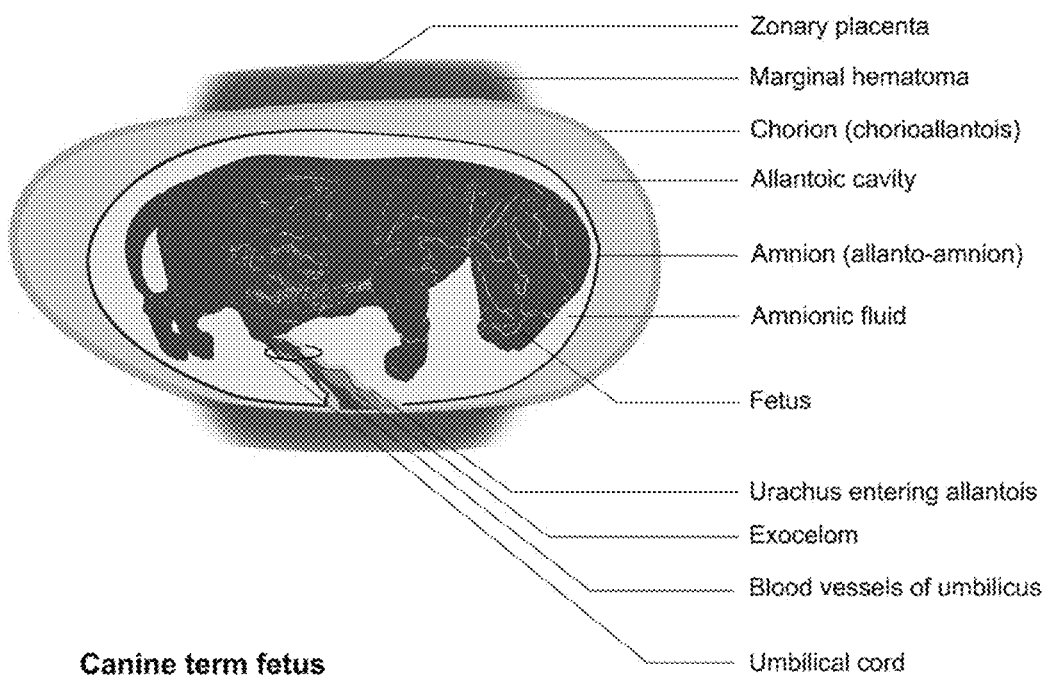
FIG. 2A shows a canine placenta and the different sacs and fluid.
Figure 2B:
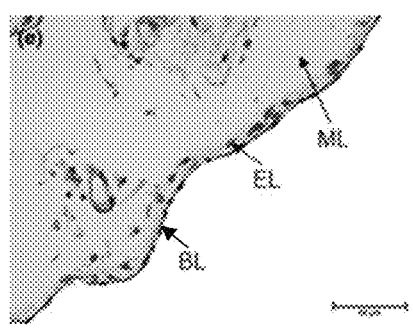
FIG. 2B and FIG. 2C shows the histology (FIG. 2B) and schematic view (FIG. 2C) of the amniotic membrane (allantoamnion) in dogs. EL: epithelial layer, BL: basal layer, ML: mesenchymal layer (i.e., stromal layer).
Figure 2C:
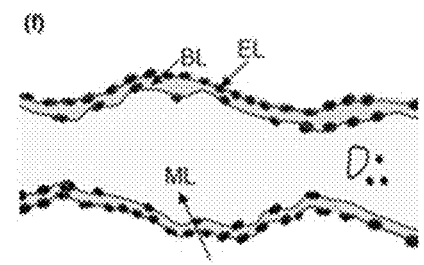
Figure 4A:
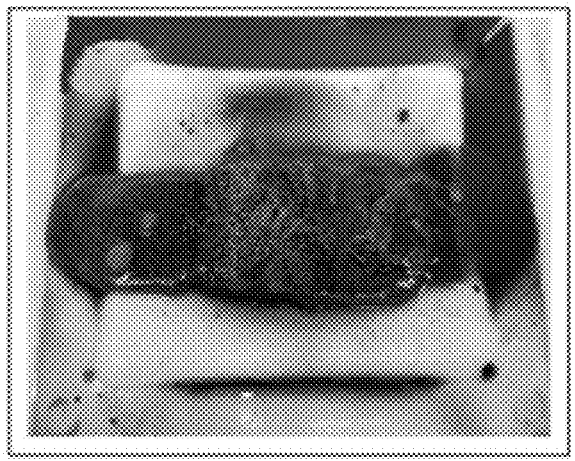
FIG. 4A shows an incoming canine placental tissue, prior to processing with the present invention.
Figure 4B:
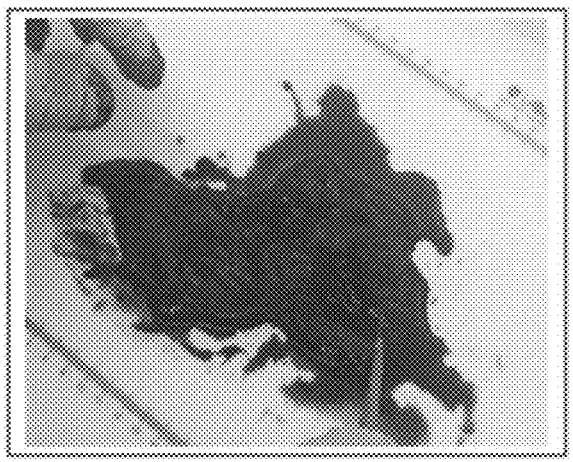
FIG. 4B shows isolation of the allantoamnion sac from the whole canine placenta.
Figure 4C:
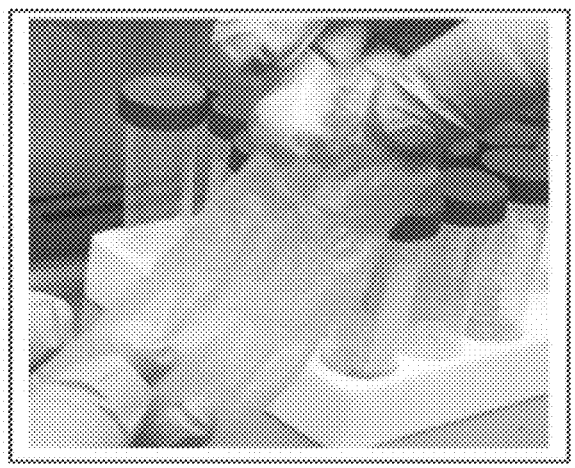
FIG. 4C shows the allantoamnion membrane after processing with the present invention.
Figure 4D:
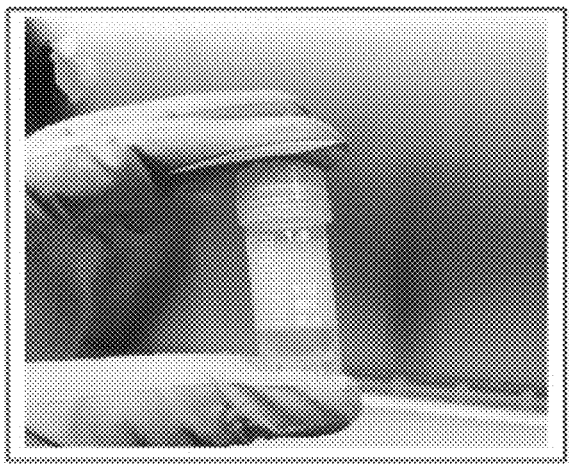
FIG. 4D shows canine-specific allantoamnion clear liquid finished product produced with and of the present invention.
Figure 5:
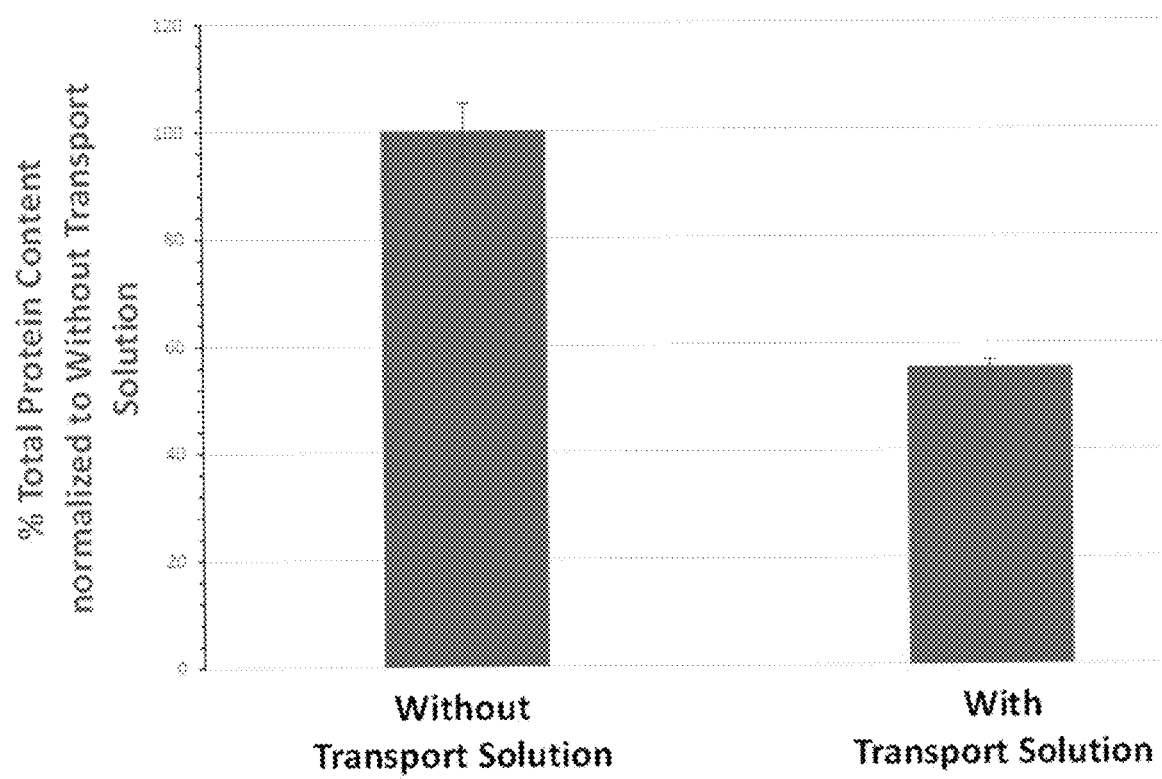
FIG. 5 shows that approximately 40% more proteins are retained in the allantoamnion membrane of the placenta when transported without a transport solution, according to the methods of the present invention, as compared to when the placenta is transported with a transport solution.
Figure 6A:
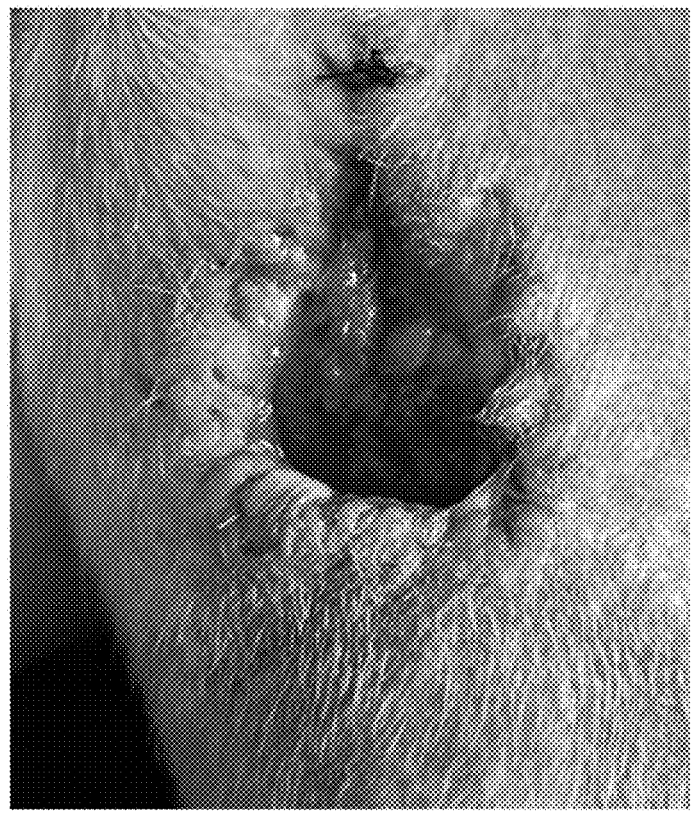
FIG. 6A shows a canine chest wound on the day of subcutaneous injection with 2.0 mL of a canine-specific therapeutic composition of the present invention.
Figure 6B:
FIG. 6B shows a canine chest wound 9 days after subcutaneous injection with 2.0 mL of a canine-specific therapeutic composition of the present invention.
Figure 6C:
FIG. 6C shows a canine chest wound 14 days after the subcutaneous injection with 2.0 mL of a canine-specific therapeutic composition of the present invention.
Figure 7A:
FIG. 7A shows a canine abdominal thermal wound before injection with 2.0 mL of a canine-specific therapeutic composition of the present invention.
Figure 7B:
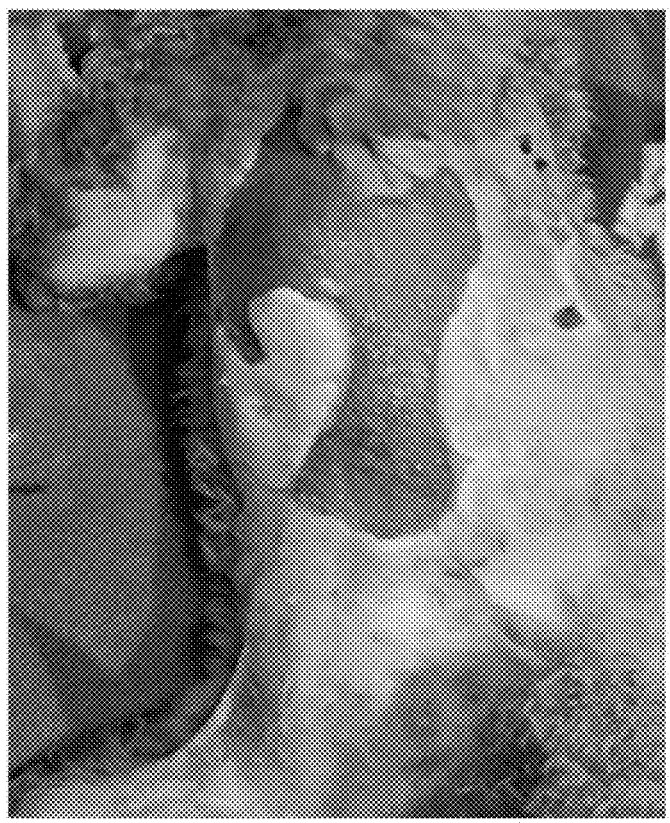
FIG. 7B shows a canine abdominal thermal wound on the day of subcutaneous injection with 2.0 mL of a canine-specific therapeutic composition of the present invention.
Figure 7C:
FIG. 7C shows a canine abdominal thermal wound 2 weeks after subcutaneous injection with 2.0 mL of a canine-specific therapeutic composition of the present invention.
Figure 7D:
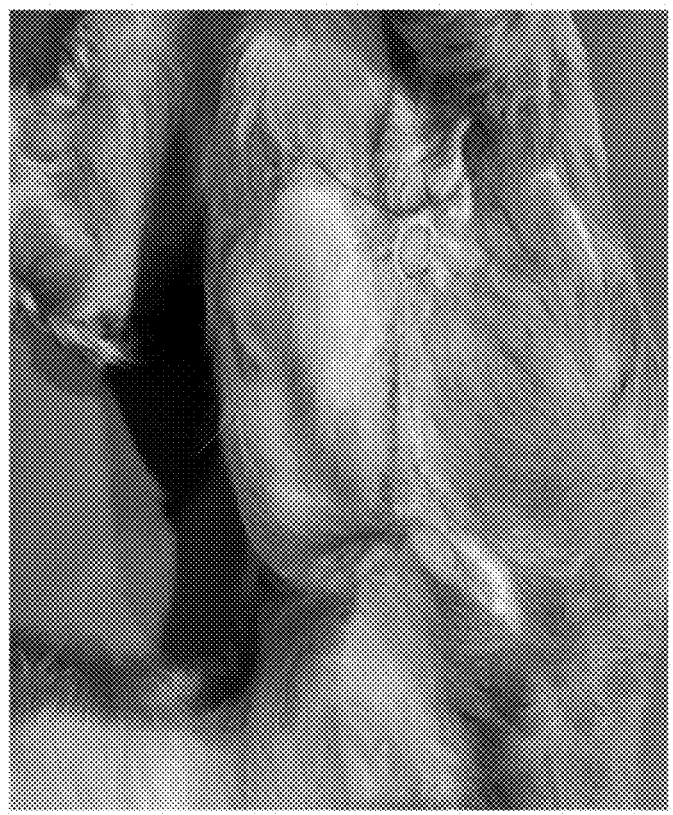
FIG. 7D shows a canine abdominal thermal wound 8 weeks after subcutaneous injection with 2.0 mL of a canine-specific therapeutic composition of the present invention.
Figure 8A:
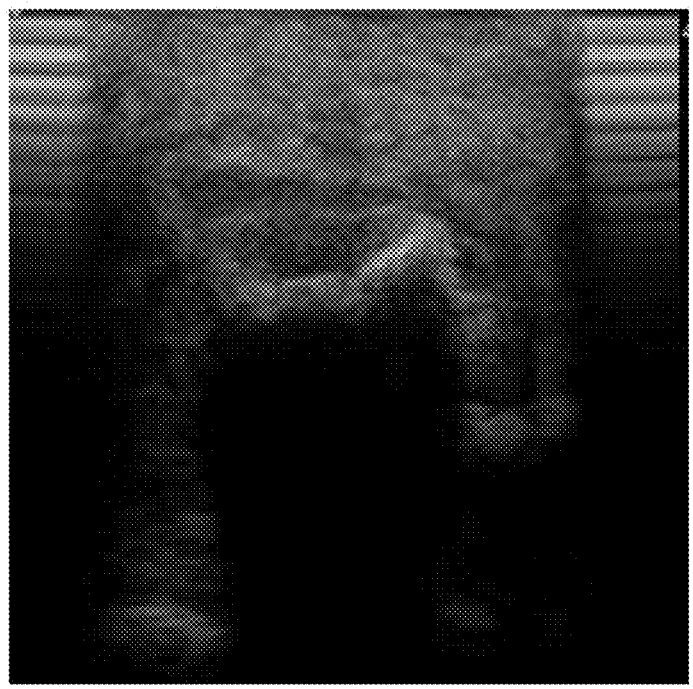
FIG. 8A shows a canine calcanean tendon lesion before injection with 1.0 mL of a canine-specific therapeutic composition of the present invention.
Figure 8B:
FIG. 8B shows a canine calcanean tendon lesion 1 month after injection with 1.0 ml of a canine-specific therapeutic composition of the present invention.
Figure 8C:
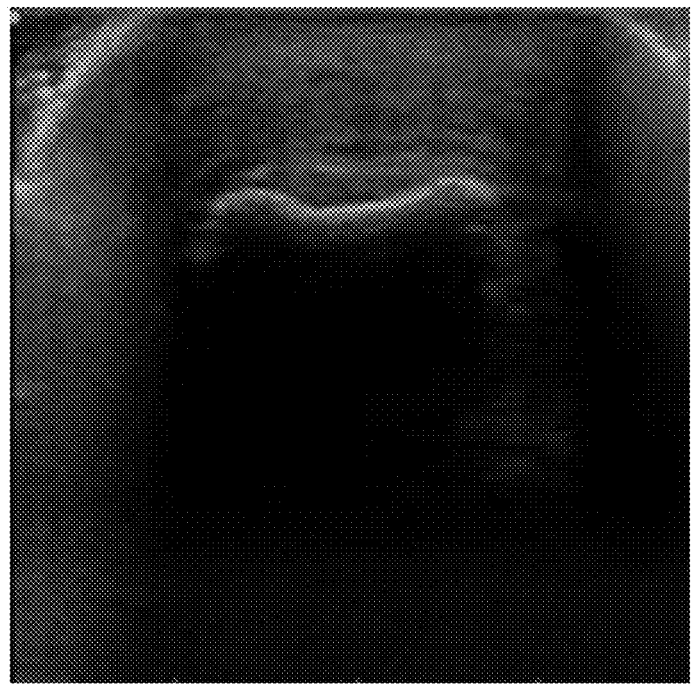
FIG. 8C shows a canine calcanean tendon lesion 2 months after injection with 1.0 ml of a canine-specific therapeutic composition of the present invention.

Referring now to FIGS. 1, 2A, 2B, 2C, 3, 4A, 4B, 4C, 4D, 5, 6A, 6B, 6C, 7A, 7B, 7C, 7D, 8A, 8B, and 8C, the present invention features methods for processing canine placental tissues into a clear, safe, and physiologically and biologically active liquid product that may be delivered via injection or any other therapeutically appropriate route of administration. Additionally, the present invention features methods for treating canine ailments using the canine-specific therapeutic composition produced and described here.

The present invention features a canine-specific therapeutic composition. In some embodiments, the composition comprises placental tissue and a working solution. In other embodiments, the placental tissue is canine-specific placental tissue. In some embodiments, the placental tissue comprises an allantoamnion membrane, an chorioallantois membrane, an umbilical cord, or a combination thereof. In some embodiments, the allantoamnion membrane comprises amniotic fluid. In some embodiments, the chorioallantois membrane comprises allantoic fluid.

Other placental tissue may be used in accordance with the methods and compositions as described herein.

In some embodiments, compositions described herein further comprise allantoamnion membrane particles, chorioallantois membrane particles, umbilical cord, or a combination thereof. In other embodiments, the compositions described herein further comprise amniotic fluid, allantoic fluid, or a combination thereof. In other embodiments, the compositions described herein further comprise cells from the amniotic fluid, allantoic fluid, or a combination thereof.

As used herein, a "working solution" refers to a solution comprising Plasma-Lyte A. In other embodiments, the working solution may also comprise NaCl solution, a phosphate buffer, any other isotonic solutions, hypertonic solutions, DMEM, water, or a combination thereof. In further embodiments, the working solution may further comprise a cryopreservative, a stabilizer, buffers, collagen, hyaluronic acid, antimicrobial agents such as antibiotics or antifungal agents, surfactants, pH modifiers, proteins, amniotic fluid, allantoic fluid or a combination thereof.

The present invention may further feature a canine-specific therapeutic composition. In some embodiments, the composition comprises an allantoamnion membrane and a working solution. In other embodiments, the allantoamnion membrane is a canine-specific allantoamnion membrane. In some embodiments, the allantoamnion comprises allantoamnion particles.

In some embodiments, the allantoamnion comprises three layers. In some embodiments, the three layers of the allantoamnion comprise a first layer, a second layer, and a third layer. The first layer and the third layer comprise an epithelial layer and a basement membrane layer and the second layer comprises a mesenchymal (i.e., stromal) layer. In some embodiments, all three layers of the allantoamnion are utilized in the compositions described herein. In some embodiments, the first layer, the second layer, the third layer or a combination thereof are utilized in the composition described herein. In some embodiments, the mesenchymal layer is a matrix comprising blood vessels. In some embodiments, the blood vessels are removed from the mesenchymal layer. In some embodiments, the blood vessels are removed from the mesenchymal layer with forceps. In some embodiments, the forceps are used to pluck the blood vessels out of the mesenchymal layer. In other embodiments, the blood vessels are removed from the mesenchymal layer by separating the two epithelial and basal layers and removing (i.e., peeling off) the blood vessels. In some embodiments, the two epithelial and basal layers are put back together.

In some embodiments, compositions described herein are free of blood vessels. In other embodiments, the compositions described herein are mostly free of blood vessels. In further embodiment, the compositions described herein comprises blood vessels. Without wishing to limit the present invention to any theory or mechanism it is believed that the removal of the blood vessels mitigates the risk of a canine patient having an immunogenic response towards the composition.

In some embodiments, compositions described herein are free or substantially free of contaminants. In some embodiments, the contaminants are blood-related components. In some embodiments, the contaminants are immunogenic blood components. In some embodiments, the contaminants are uteroverdin. In some components, the contaminants are products of hemoglobin breakdown. In some embodiments, the contaminants are red blood cells. In some embodiments, the contaminants are immunogenic. In some embodiments, the contaminants are immunogenic blood-related components. Without wishing to limit the present invention to any theory or mechanism it is believed that the removal of contaminants mitigates the risk of a canine patient having an immunogenic response towards the composition, thereby improving canine-patient recipient safety and increasing the effectiveness of the compositions by preventing graft rejection.

In some embodiments, compositions described herein do not elicit an immune-mediated reaction upon introduction into a canine allograft recipient. In some embodiments, compositions described herein do not elicit a clinically significant immune-mediated reaction upon introduction into a canine allograft recipient. In some embodiments, compositions described herein do not elicit an alloimmunization response upon introduction into a canine allograft recipient. In some embodiments, compositions described herein do not elicit a clinically significant alloimmunization response upon introduction into a canine allograft recipient. Without wishing to limit the present invention to any theory or mechanism it is believed that these properties of the present invention mitigate the risk of a canine patient having an immunogenic and/or alloimmunization response towards the composition, thereby improving canine-patient recipient safety and increasing the effectiveness of the compositions by preventing graft rejection.

In some embodiments, compositions described herein are liquids or suspensions substantially free of green color. In some embodiments, the compositions are a substantially colorless liquid or suspension. In some embodiments, the compositions are a substantially clear liquid or suspension.

In some embodiments, the compositions are a substantially clear and colorless liquid or suspension. In some embodiments, the compositions are a substantially cloudy and colorless liquid or suspension. Without wishing to limit the present invention to any theory or mechanism it is believed that these properties of the present invention represent removal of contaminants from the compositions of the present invention, thus mitigating the risk of a canine patient having an immunogenic and/or alloimmunization response towards the composition, thereby improving canine patient-recipient safety and increasing the effectiveness of the compositions by preventing graft rejection. In some embodiments, the compositions further comprise about 2 $cm^2$ of allantoamnion membrane per about 1 mL of working solution. Without wishing to limit the present invention to any theory or mechanism, it is believed that this ratio may produce fewer adverse effects and achieve superior therapeutic results compared to other ratios.

In some embodiments, the compositions described herein comprise protein. In some embodiments, the proteins have anti-inflammatory properties, antifibrotic properties, antibacterial properties, anti-fungal properties, healing properties, repairing properties, immunoregulatory properties, anti-cancer properties, or a combination thereof. In some embodiments, the compositions described herein are clear, safe, and physiologically and biologically active.

In some embodiments, the proteins may include but are not limited to IL1-ra, IL-2, IL-4, IL-6, IL-8, IL-10, MCP-1, VEGF, TIMP-1, TIMP-2, TIMP-3, TIMP-4, IGF, EGF, FGF, TGFb1, alpha-2-microglobulin, hyaluronic acid, proteoglycans, collagen, fibronectin, laminin and the like.

In some embodiments, the compositions described herein are injectable. In other embodiments, the compositions, described herein are for topical use. In other embodiments, the compositions described herein may be applied intravenously or intra arterially. In other embodiments, the compositions described herein may be used intraoperatively. In other embodiments, the compositions described herein may be in the form of a liquid or gel, ointment, polymer, cream, lotion, foam, oil, paste, capsule, tablet, or lyophilized.

In some embodiments, the present invention features a method of treating cancer in a canine. In some embodiments, the method comprises administering a therapeutic amount of a composition as described herein, to the canine in need thereof. In other embodiments, the present invention features a method of preventing cancer in a canine. In some embodiments, the method comprises administering a therapeutic amount of a composition as described herein, to the canine in need thereof.

In some embodiments, the canine-specific therapeutic compositions described herein are used as regenerative products. In other embodiments, the canine-specific therapeutic compositions described herein are a biodegradable and/or bioabsorbable tissue scaffold. Without wishing to limit the present invention to any theory or mechanism it is believed that after the canine-specific therapeutic composition is injected into a target site, proteins, cellular excretions, cellular derivatives, and extracellular matrix components from the composition will elute out/be absorbed into the native surrounding tissue. Also, the membrane particles may act as a scaffold to facilitate migration of the surrounding cells, reinforce adhesion of the basal epithelium, promote cellular differentiation, and prevent apoptosis.

In some embodiments, compositions described herein may be used to treat various canine ailments. Non-limiting examples of canine ailments that may be treated with compositions described herein include but are not limited to cancer, benign tumors, joint diseases, soft tissue lesions, inflammatory diseases, immunological diseases, neurological diseases, skin wound and repair (e.g. burns, necrosis, scarring, skin ulcers and venous ulcers), ocular wounds and repair (e.g. glaucoma, ocular ulcers, corneal ulcers, conjunctival scleral and lid and orbital rim reconstruction), coronary wounds and repair (e.g. coronary bypass, heart valve repair and replacement, vein repair and artery repair), nerve injuries, spinal injuries, muscle tears, organ diseases, among others. In other embodiments, compositions described herein may have anticancer effects. In other embodiments, compositions described herein may have immunoregulatory effects.

The present invention features a method of producing a canine-specific therapeutic composition. In some embodiments, the method comprises obtaining an allantoamnion membrane. In some embodiments, the method comprises micronizing said allantoamnion membrane. In other embodiments, the method comprises resuspending the micronized allantoamnion membrane into a working solution to create a canine-specific therapeutic composition.

In some embodiments, obtaining an allantoamnion membrane comprises obtaining a whole placenta and dissecting the whole canine placenta to obtain the allantoamnion membrane. In some embodiments, the whole placenta is a whole canine placenta. In some embodiments, the methods described herein further comprise processing the allantoamnion membrane to retain all layers of the allantoamnion membrane. In other embodiments, the methods described herein further comprise processing the allantoamnion membrane to retain one or more layers of the allantoamnion membrane. In further embodiments, the methods described herein further comprise processing the allantoamnion membrane to retain two or more layers of the allantoamnion membrane.

In some embodiments, the methods described herein further comprise processing the allantoamnion membrane to retain at least one layer of the allantoamnion membrane. In other embodiments, the methods described herein further comprise processing the allantoamnion membrane to retain at least two layers of the allantoamnion membrane.

In some embodiments, processing the allantoamnion membrane further comprises removing the blood vessels. In some embodiments, the methods described herein further comprise rinsing to remove blood or contaminants and drying the allantoamnion membrane. In other embodiments, the methods described herein further comprise cryofracturing the allantomanion membrane to produce allantomanion particles. In other embodiments, the methods described herein further comprise resuspending the allantoamnion particles in a working solution to produce a canine-specific therapeutic composition. In other embodiments, the methods described herein further comprise freezing the canine-specific therapeutic composition. In some embodiments, freezing the canine-specific therapeutic composition preserves proteins.

The present invention may further feature a method of producing a canine-specific therapeutic composition. In some embodiments, the method comprises obtaining a whole canine placenta. In some embodiments, the method comprises dissecting the whole canine placenta and retaining an allantoamnion membrane. In some embodiments, the method comprises rinsing the allantoamnion membrane and drying the allantoamnion membrane. In some embodiments, the method comprises micronizing the aforementioned allantoamnion membrane and resuspending the micronized allantoamnion membrane into a working solution to create a canine-specific therapeutic composition. In other embodiments, the method further comprises freezing the canine-specific therapeutic composition to preserve proteins.

In some embodiments, the methods described herein further comprise lyophilization of the canine-specific therapeutic composition.

In some embodiments, the tissue (e.g., placental tissue or allantoamnion membrane) can be frozen prior to the micronizing process. The freezing step can occur by any suitable cooling process. For example, the tissue can be flash-frozen using liquid nitrogen. Alternatively, the material can be placed in an isopropanol/dry ice bath or can be flash-frozen in other coolants. Additionally, the material can be placed in a freezer and allowed to equilibrate to the storage temperature more slowly, rather than being flash-frozen. The tissue can be stored at any desired temperature. For example, −20° ° C. or −80° C., or other temperatures can be used for storage. In other embodiments, the methods described herein further comprises storing the canine-specific therapeutic composition at room temperature. In some embodiments, the methods described herein further comprise storing the canine-specific therapeutic composition at refrigerator temperature. In further embodiments, the methods described herein further comprise storing the canine-specific therapeutic composition below 0° C. (e.g., −20° C. or −80° C.).

In other embodiments, the tissue (e.g., placental tissue or allantoamnion membrane) can be decontaminated prior to or after the micronizing process. In one aspect, the premixed antibiotic solution comprising a cocktail of antibiotics such as Gentamicin and Streptomycin can be added and mixed with the tissue (e.g., placental tissue or allantoamnion membrane). In another aspect, 0.1-10% Triton-X or alcohol such as 70% isopropanol may be used. In other aspects, the tissue can be exposed to UV.

In some embodiments, the whole canine placenta is obtained after a live birth. In other embodiments, the whole canine placenta is obtained after a scheduled c-section.

In some embodiments, the whole canine placenta is transported without a transport solution (i.e., a saline solution). In some embodiments, the whole canine placenta is transported wet. In other embodiments, the whole canine placenta is transported wet in a jar. In further embodiments, the placenta is removed from the canine and placed into a jar and then transported. Without wishing to limit the present invention to any theories or mechanisms it is believed that transporting the whole canine placenta without a transport solution (e.g., saline solution) advantageously provides for an increase in retained proteins within the placenta as compared to a canine placenta transported in a transport solution. When transported in a transport solution (e.g., a saline solution) proteins (~40%) elute out of the placental membranes and into the transport solution. In certain embodiments, the whole canine placenta is transported in a transport solution (i.e., a saline solution).

In some embodiments, the method further comprises processing the allantoamnion membrane to retain all three layers of the allantoamnion membrane. In some embodiments, the blood vessels are removed from the allantoamnion membrane. In some embodiments, the allantoamnion membrane further comprises amniotic fluid.

In certain embodiments, the allantoamnion membrane is rinsed for 10 seconds. In other embodiments, the allantoamnion membrane is rinsed for about 5 seconds, or about 10 seconds, or about 15 seconds, or about 20 seconds, or about 25 seconds, or about 30 seconds, or about 35 seconds, or about 40 seconds, or about 45 seconds, or about 50 seconds, or about 55 seconds, or about 60 seconds, or about 65 seconds, or about 70 seconds, or about 75 seconds, or about 80 seconds, or about 85 seconds, or about 90 seconds. Without wishing to limit the present invention to any theory or mechanism it is believed that gently rinsing the allantoamnion membrane (instead of washing) allows for the retention of all three layers (i.e., a first epithelial and basal layer, a mesenchymal layer, and a second epithelial and basal layer).

In certain embodiments, the allantoamnion membrane is dried for 1 hour. In other embodiments, the allantoamnion membrane is dried for about 15 minutes, or about 30 minutes, or about 45 minutes, or about 60 minutes, or about 75 minutes, or about 90 minutes, or about 105 minutes, or about 2 hours, or about 2.25 hours, or about 2.5 hours, or about 2.75 hours, or about 3 hours. In some embodiments, the allantoamnion membrane is dried for more than 3 hours. In some embodiments, the allantoamnion membrane is air dried. In other embodiments, the allantoamnion membrane is air dried at room temperature.

In certain embodiments, the canine-specific therapeutic composition produced has a ratio of 2 $cm^2/mL$ of working solution. In other embodiments, the canine-specific therapeutic composition produced has a ratio of about 0.25 $cm^2/mL$ of working solution, or about 0.5 $cm^2/mL$ of working solution, or about 1.0 $cm^2/mL$ of working solution, or about 1.5 $cm^2/mL$ of working solution, or about 2.0 $cm^2/mL$ of working solution, or about 2.5 $cm^2/mL$ of working solution, or about 3.0 $cm^2/mL$ of working solution, or about 3.5 $cm^2/mL$ of working solution, or about 4.0 $cm^2/mL$ of working solution, or about 4.5 $cm^2/mL$ of working solution, or about 5.0 $cm^2/mL$ of working solution, or about 7.5 $cm^2/mL$ of working solution, or about 10.0 $cm^2/mL$ of working solution, or about 12.5 $cm^2/mL$ of working solution, or about 15.0 $cm^2/mL$ of working solution, or about 17.5 $cm^2/mL$ of working solution, or about 20.0 $cm^2/mL$ of working solution, or about 22.5 $cm^2/mL$ of working solution, or about 25.0 $cm^2/mL$ of working solution, or about 27.5 $cm^2/mL$ of working solution, or about 30.0 $cm^2/mL$ of working solution.

The present invention may further feature a method of treating or preventing cancer in a canine. In some embodiments, the method comprises administering a therapeutic amount of canine-specific therapeutic composition comprising placental tissue and a working solution.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The following embodiments are intended to be illustrative only and not to be limiting in any way.

Embodiment 1: A canine-specific therapeutic composition, the composition comprising placental tissue in a working solution.

Embodiment 2: The composition of embodiment 1, wherein the placental tissue is canine-specific placental tissue.

Embodiment 3: The composition of embodiment 1 or embodiment 2, wherein the placental tissue comprises an allantoamnion membrane, an chorioallantois membrane, umbilical cord, or a combination thereof.

Embodiment 4: The composition of embodiment 3, wherein the allantoamnion membrane further comprises amniotic fluid.

Embodiment 5: The composition of embodiment 3, wherein the chorioallantois membrane further comprises allantoic fluid.

Embodiment 6: The composition of any one of embodiments 1-5, further comprising allantoamnion membrane particles, chorioallantois membrane particles, umbilical cord particles, or a combination thereof.

Embodiment 7: The composition of any one of embodiments 1-6, further comprising amniotic fluid, allantoic fluid, or a combination thereof.

Embodiment 8: The composition of any one of embodiments 1-7, further comprising amniotic fluid cells, allantoic fluid cells, mesenchymal stem cells, or a combination thereof.

Embodiment 9: A canine-specific therapeutic composition comprising an allantoamnion membrane in a working solution.

Embodiment 10: The composition of embodiment 9, wherein the allantoamnion membrane is canine-specific allantoamnion membrane.

Embodiment 11: The composition of embodiment 9 or embodiment 10, wherein the allantoamnion comprises allantoamnion particles.

Embodiment 12: The composition of any one of embodiments 1-11, wherein the composition is free of blood vessels.

Embodiment 13: The composition of any one of embodiments 1-11, wherein the composition comprises blood vessels.

Embodiment 14: The composition of any one of embodiments 1-13, wherein the composition comprises proteins.

Embodiment 15: The composition of embodiment 14, wherein the proteins have anti-inflammatory properties, antifibrotic properties, healing properties, repairing properties, immunoregulatory properties, anti-cancer properties, or a combination thereof.

Embodiment 16: The composition of any one of embodiments 1-15, wherein the composition is physiologically and biologically active.

Embodiment 17: The composition of any one of embodiments 1-16, wherein the composition is injectable.

Embodiment 18: The composition of any one of embodiments 1-16, wherein the composition is administered topically.

Embodiment 19: The composition of any one of embodiments 1-16, wherein the composition is administered intravenously or intraarterially.

Embodiment 20: The composition of any one of embodiments 1-16, wherein the composition is administered intraoperatively.

Embodiment 21: The composition of any one of embodiments 1-16, wherein the composition is administered intra articularly or intramuscularly.

Embodiment 22: The composition of any one of embodiments 1-16, wherein the composition is administered via an intraligamentary or intratendon injection.

Embodiment 23: The composition of any one of embodiments 1-22, wherein the composition is used to treat cancer, benign tumors, joint diseases, joint injuries, soft tissue lesions, inflammatory diseases, immunological diseases, neurological diseases, skin wounds, ocular wounds, coronary wounds, nerve injuries, spinal injuries, muscle tears or organ diseases in canines in need thereof.

Embodiment 24: The composition of embodiment 23, wherein skin wounds comprise burns, necrosis, scarring, skin ulcers and venous ulcers.

Embodiment 25: The composition of embodiment 23, wherein ocular wounds comprise glaucoma, ocular ulcers, corneal ulcers, conjunctival scleral or lid and orbital rim reconstruction.

Embodiment 26: The composition of embodiment 23, wherein coronary wounds comprise coronary bypass, heart valve repair and replacement, vein repair and artery repair.

Embodiment 27: The composition of any one of embodiments 1-22, wherein the composition is used for skin repair, ocular repair or coronary repair.

Embodiment 28: A method of treating cancer in a canine, the method comprising administering a therapeutic amount of a composition according to any one of embodiments 1-22, to the canine in need thereof.

Embodiment 29: A method of preventing cancer in a canine, the method comprising administering a therapeutic amount of a composition according to any one of embodiments 1-22, to the canine in need thereof.

Embodiment 30: The composition of any one of embodiments 1-27, wherein the composition is substantially free of uteroverdin.

Embodiment 31: The composition of any one of embodiments 1-27, wherein the composition is substantially free of products of hemoglobin breakdown.

Embodiment 32: The composition of any one of embodiments 1-27, wherein the composition is substantially free of red blood cells.

Embodiment 33: The composition of any one of embodiments 1-27, wherein the composition is substantially free of contamination with blood-related components.

Embodiment 34: The composition of any one of embodiments 1-27, wherein the composition is substantially free of immunogenic components.

Embodiment 35: The composition of any one of embodiments 1-27, wherein the composition is substantially free of immunogenic blood components.

Embodiment 36: The composition of any one of embodiments 1-27, wherein the composition does not elicit a clinically significant immune-mediated reaction upon introduction into a canine allograft recipient.

Embodiment 37: The composition of any one of embodiments 1-27, wherein the composition does not elicit a clinically significant alloimmunization response upon introduction into a canine allograft recipient.

Embodiment 38: The composition of any one of embodiments 1-27, wherein the composition is a liquid or suspension substantially free of green color.

Embodiment 39: The composition of any one of embodiments 1-27, wherein the composition is a substantially colorless liquid or suspension.

Embodiment 40: The composition of any one of embodiments 1-27, wherein the composition is a substantially clear liquid or suspension.

Embodiment 41: The composition of any one of embodiments 1-27, wherein the composition is a substantially clear and colorless liquid or suspension.

Embodiment 42: The composition of any one of embodiments 1-27, wherein the composition is a substantially cloudy and colorless liquid or suspension.

Embodiment 43: The composition of embodiments 1 or 2, wherein the composition further comprises about 2 cm² of an allantoamnion membrane per about 1 mL of the working solution.

Embodiment 44: A method of producing a canine-specific therapeutic composition, the method comprising:
 a. obtaining an allantoamnion membrane;
 b. rinsing and drying the allantoamnion membrane;
 c. micronizing said allantoamnion membrane; and
 d. resuspending the micronized allantoamnion membrane into a working solution to create a canine-specific therapeutic composition.

Embodiment 45: The method of embodiment 44, wherein obtaining the allantoamnion membrane comprises obtaining a whole placenta and dissecting the whole canine placenta to obtain the allantoamnion membrane.

Embodiment 46: The method of embodiment 45, wherein the whole placenta is a whole canine placenta.

Embodiment 47: The method of embodiment 44, further comprising processing the allantoamnion membrane to retain all layers of the allantoamnion membrane.

Embodiment 48: The method of embodiment 44, further comprising processing the allantoamnion membrane to retain one or more layers of the allantoamnion membrane.

Embodiment 49: The method of embodiment 44, further comprising processing the allantoamnion membrane to retain two or more layers of the allantoamnion membrane.

Embodiment 50: The method of embodiments 47-49, wherein processing the allantoamnion membrane further comprises partially removing the blood vessels.

Embodiment 51: The method of embodiments 47-49, wherein processing the allantoamnion membrane further comprises removing the blood vessels.

Embodiment 52: The method of embodiment 44, further comprising rinsing and drying the allantoamnion membrane.

Embodiment 53: The method of embodiment 44, further comprising cryofracturing the allantomanion membrane to produce allantomanion particles.

Embodiment 54: The method of embodiment 53, wherein the allantomanion particles are added to a working solution to produce a canine-specific therapeutic composition.

Embodiment 55: The method of embodiment 44, further comprising freezing the canine-specific therapeutic composition.

Embodiment 56: The method of embodiment 55, wherein freezing the canine-specific therapeutic composition preserves proteins.

Embodiment 57: The method of embodiment 44, further comprising lyophilization of the canine-specific therapeutic composition.

Embodiment 58: The method of embodiment 44, further comprising storing the canine-specific therapeutic composition at room temperature.

Embodiment 59: The method of embodiment 44, further comprising storing the canine-specific therapeutic composition at refrigerator temperature.

Embodiment 60: The method of embodiment 44, further comprising obtaining the allantoamnion membrane by transporting the allantoamnion membrane without a transport solution.

Embodiment 61: A method of producing a canine-specific therapeutic composition, the method comprising:
 a. obtaining a whole canine placenta;
 b. dissecting the whole canine placenta and retaining an allantoamnion membrane;
 c. processing the allantoamnion membrane to retain one or more layers of the allantoamnion membrane;
 d. rinsing and drying the allantoamnion membrane;
 e. micronizing said allantoamnion membrane;
 f. resuspending the micronized allantoamnion membrane into a working solution to create a canine-specific therapeutic composition; and
 g. freezing the canine-specific therapeutic composition to preserve proteins.

Embodiment 62: The method of embodiment 61, further comprising processing the allantoamnion membrane to retain all layers of the allantoamnion membrane.

Embodiment 63: The method of embodiment 61, further comprising lyophilization of the canine-specific therapeutic composition.

Embodiment 64: The method of embodiment 61, further comprising storing the canine-specific therapeutic composition at room temperature.

Embodiment 65: The method of embodiment 61, further comprising storing the canine-specific therapeutic composition at refrigerator temperature.

Embodiment 66: The method of embodiment 61, further comprising obtaining the allantoamnion membrane by transporting the allantoamnion membrane without a transport solution.

Embodiment 67: The method of any one of embodiments 44-66, wherein the allantoamnoin membrane further comprises amniotic fluid.

Embodiment 68: The method of any one of embodiments 44-67, wherein the allantoamnion membrane is rinsed for 10 seconds.

Embodiment 69: The method of any one of embodiments 44-68, wherein the allantoamnion membrane is dried for 1 hour.

Embodiment 70: The method of any one of embodiments 44-69, wherein the canine-specific therapeutic composition has a ratio of 0.25 cm²/mL to 30 cm²/mL of working solution.

Embodiment 71: The method of any one of embodiments 44-70, wherein the canine-specific therapeutic composition has a ratio of 1.0 cm²/mL to 5.0 cm²/mL of working solution.

Embodiment 72: A method of treating cancer in a canine, the method comprising administering a therapeutic amount of canine-specific therapeutic composition comprising placental tissue in a working solution.

Embodiment 73: A method of preventing cancer in a canine, the method comprising administering a therapeutic amount of canine-specific therapeutic composition comprising placental tissue in a working solution.

Embodiment 74: The method of embodiment 72 or embodiment 73, wherein the placental tissue is canine-specific placental tissue.

Embodiment 75: The method of any one of embodiments 72-74, wherein the placental tissue comprises an allantoamnion membrane, a chorioallantois membrane, umbilical cord, or a combination thereof.

Embodiment 76: The method of any one of embodiments 72-75, wherein the canine-specific therapeutic composition comprises allantoamnion membrane particles.

Embodiment 77: A method of treating cancer in a canine, the method comprising administering a therapeutic amount of canine-specific therapeutic composition comprising allantoamnion membrane particles in a working solution.

Embodiment 78: A method of preventing cancer in a canine, the method comprising administering a therapeutic amount of canine-specific therapeutic composition comprising allantoamnion membrane particles in a working solution.

Embodiment 79: A method of treating a joint disease in a canine, the method comprising administering a therapeutic amount of canine-specific therapeutic composition comprising placental tissue in a working solution.

Embodiment 80: A method of treating a joint injury in a canine, the method comprising administering a therapeutic amount of canine-specific therapeutic composition comprising placental tissue in a working solution.

Embodiment 81: A method of treating a soft tissue injury in a canine, the method comprising administering a therapeutic amount of canine-specific therapeutic composition comprising placental tissue in a working solution.

Embodiment 82: The method of any one of embodiments 79-81, wherein the placental tissue is canine-specific placental tissue.

Embodiment 83: The method of any one of embodiments 79-82, wherein the placental tissue comprises an allantoamnion membrane, an chorioallantois membrane, umbilical cord, or a combination thereof.

Embodiment 84: The method of any one of embodiments 79-83, wherein the canine-specific therapeutic composition comprises allantoamnion membrane particles.

What is claimed is:

1. A canine-specific therapeutic composition comprising a micronized canine-specific allantoamnion membrane in a solution;
wherein the composition is substantially free of blood-related contaminants and/or uteroverdin.

2. The composition of claim 1, further comprising a micronized canine-specific chorioallantois membrane, micronized canine-specific umbilical cord, or a combination thereof.

3. The composition of claim 1, further comprising micronized canine-specific allantoamnion membrane particles, micronized canine-specific chorioallantois membrane particles, micronized canine-specific umbilical cord particles, or a combination thereof.

4. The composition of claim 1, further comprising canine-specific amniotic fluid, canine-specific allantoic fluid, or a combination thereof.

5. The composition of claim 1, further comprising canine-specific amniotic fluid cells, canine-specific allantoic fluid cells, canine-specific mesenchymal stem cells, or a combination thereof.

6. The composition of claim 1, wherein the composition comprises proteins.

7. The composition of claim 6, wherein the proteins have anti-inflammatory properties, antifibrotic properties, healing properties, repairing properties, immunoregulatory properties, anti-cancer properties, or a combination thereof.

8. The composition of claim 1, wherein the composition is physiologically and biologically active.

9. The composition of claim 1, wherein the composition is injectable.

10. The composition of claim 1, wherein the composition is administered topically.

11. The composition of claim 1, wherein the composition is administered intravenously or intraarterially.

12. The composition of claim 1, wherein the composition is further lyophilized.

13. The composition of claim 1, wherein the composition is administered intra-articularly.

14. The composition of claim 1, wherein the composition is administered via an intraligamentary injection and/or an intratendon injection.

15. The composition of claim 1, wherein the micronized canine-specific allantoamnion membrane is micronized by cryogenic fracturing.

16. A canine-specific therapeutic composition comprising a micronized canine-specific allantoamnion membrane in a solution; wherein the composition is free of blood-related contaminants and/or uteroverdin.

17. An injectable canine-specific therapeutic composition comprising a micronized canine-specific allantoamnion membrane; wherein the composition is substantially free of blood-related contaminants and/or uteroverdin.

* * * * *